United States Patent [19]
Garrett

[11] Patent Number: 5,218,974
[45] Date of Patent: Jun. 15, 1993

[54] PENILE ERECTION AID

[76] Inventor: Clarence J. Garrett, 510 E. Main St., Morganfield, Ky. 42437

[21] Appl. No.: 763,542

[22] Filed: Sep. 23, 1991

[51] Int. Cl.$^5$ .............................................. A61F 5/37
[52] U.S. Cl. ..................................... 128/845; 128/846
[58] Field of Search ............... 128/842, 843, 845, 846, 128/883, 82.1

[56] References Cited

U.S. PATENT DOCUMENTS

| 32,842 | 7/1861 | Reynolds | 128/883 |
| 37,116 | 12/1862 | Sunderland | 128/883 |
| 427,468 | 5/1890 | Dow | 128/82.1 |
| 622,333 | 4/1899 | Dudley | 128/883 |
| 742,814 | 10/1903 | Todd | 128/82.1 |
| 976,564 | 11/1910 | Goodson | 128/845 |
| 4,942,885 | 7/1990 | Davis et al. | 128/842 |

Primary Examiner—Robert A. Hafer
Assistant Examiner—Sam Rimell
Attorney, Agent, or Firm—Fisher, Christen & Sabol

[57] ABSTRACT

A penile erection aid which is readily adaptable to the person of the user, requiring no surgical techniques, but, instead, the development of pressure in a region adaptable for producing and constricting blood flow into an initially flaccid penis. The aid is typically made from a belt which encircles the lower torso of the user and a flexible strap extending between the space within the buttocks and an encircling relationship with the base of the penis.

4 Claims, 1 Drawing Sheet

FIG. 1
FIG. 2
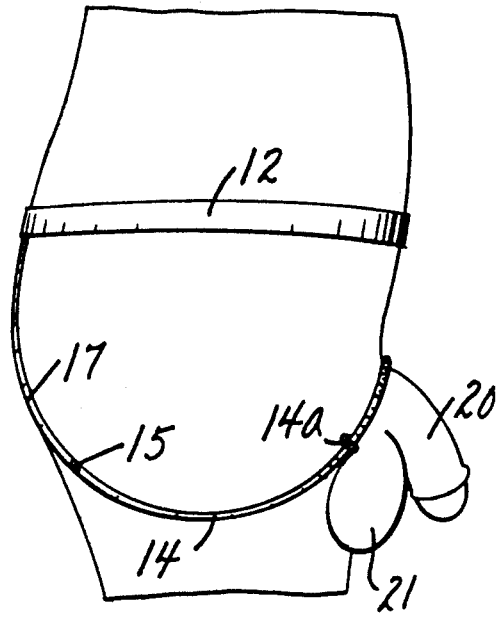
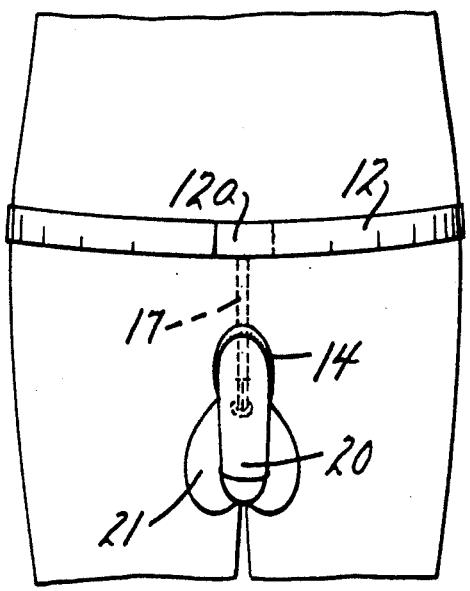
FIG. 3
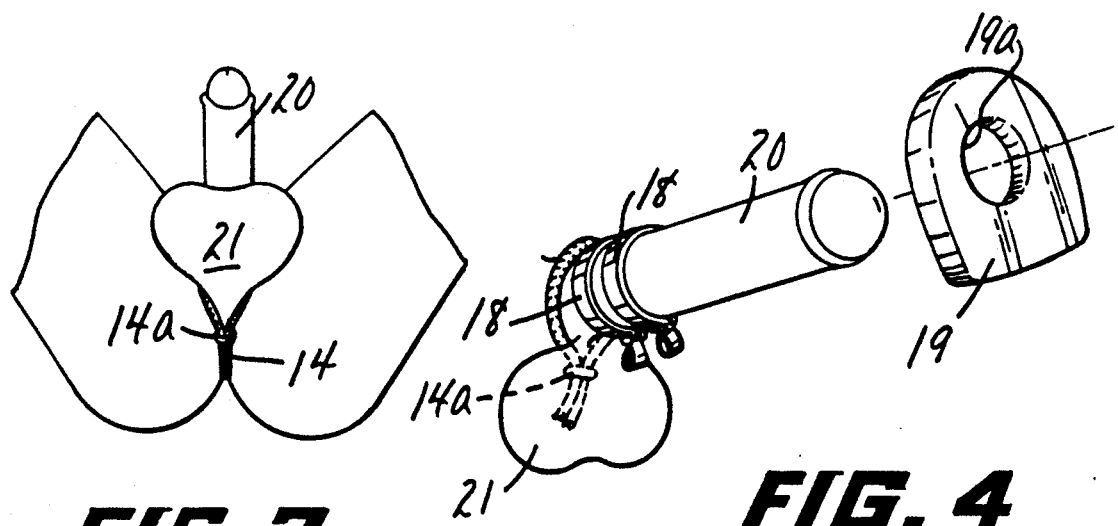
FIG. 4

PENILE ERECTION AID

BACKGROUND OF THE INVENTION

As is known, a problem oftentimes surfaces, in a male, after prostate surgery and for many other reasons, i.e. impotence and/or the inability to establish a penile erection necessary for sexual functioning. Many approaches have been developed to solve the aforesaid problem, including, by way of example, a semi-rigid implant, a malleable implant, a self-contained inflatable implant or a fully inflatable implant and/or other non-surgical devices. Each of the preceding, however, raises various objections, as, by way of further example, a problem of concealment, the actual mechanics for achieving an inflatable status and the possibility of injury or breakage in the manipulation of the mechanism for transport and/or usage.

DESCRIPTION OF THE INVENTION

The invention represents a non-surgical approach to the treatment of impotence, relying on a simple arrangement of a support belt extending about the waist or lower torso region of the user, a strap, typically fabricated from a soft yet strong material, overlying the base of the penis, i.e. in the groin or lower abdomen area, extending along both sides of the scrotum, then between the buttocks and stitched, for example, onto a elastic member which, in turn, is secured to the waist belt.

The assembly further includes an adjuster for user comfort, constrictors for limiting blood passage, and a snug fitting shield which presents an opening for the erect penis and serves to support and eliminate any unwanted pivoting effect.

Basically, the invention serves to force achieve the desired erection, where an area of principal concern is that defined by space along the sides and behind the scrotum and extending to the anus.

DESCRIPTION OF THE FIGURES

In any event, a better understanding of the principal invention will become more apparent from the following description, taken in conjunction with the accompanying drawing, wherein FIG. 1 is a view in side elevation showing an installed penile erection aid in accordance with the teachings of the present invention;

FIG. 2 is a view in front elevation, looking from right to left in FIG. 1, further detailing the invention in a use condition;

FIG. 3 is a detailed view showing the strap path at an important region for establishing pressured blood; and, FIG. 4 is a perspective view illustrating accessory items useful in the practice of the invention.

For the purposes of promoting an understanding of the principles of the invention, reference will now be made to the embodiment illustrated in the drawing and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

DESCRIPTION OF THE PREFERRED EMBODIMENT

Referring now to the figures, and particularly to FIGS. 1, 2 and 3, the penile erection aid of the invention, in a typical form, includes a belt 12 which encircles the person of the user, at the waist, or lower torso. The belt 12 is provided with a common arrangement for tensioning, as a buckle or a slide 12a.

The instant erection aid is defined by a flexible strap 14, made from a non-abrasive material, which partially encircles the base of the penis 20 in the region of the groin or lower abdomen, and an adjuster 14a which is movable to a comfort location for the user. The strap 14 follows a path on either side of the scrotum 21 and extends, side-by-side, within the space between the buttocks (see FIG. 3).

At some convenient termination point, as 15, the strap 14 is secured to a elastic member 17, as by stitching, for example, and, thereafter continues an upward path, terminating by a junction with the belt 12.

Importantly, and as particularly evident in FIG. 3, strong and continual pressure is exerted in the region or area proximate the scrotum and the anus. Thus, and with continued applied pressure, the desired penile erection is accomplished.

Referring now to FIG. 4, one or more constrictors 18 are provided for placement on the penis 20 so as to assist in maintaining the achieved erection. Moreover, a pliable shield 19, including an opening 19a through which the penis 20 is inserted, has a two-fold purpose, namely as a directional aid (for the penis 20) and for additional support during a use condition.

It should be evident, therefore, that the invention overcomes a physical problem oftentimes caused by prostate surgery, and/or other forms of impotence, plagued by many males. Pressure application is important to achieve the desired penis erection and, as stated heretofore, the region or area proximate the scrotum and the anus significantly defines a pressure creating force.

The penile erection aid described above is susceptible to various changes within the spirit of the invention, including, by way of example, material selection, i.e. the belt disposed around the lower torso of the user and/or the strap for blood flow production; the shape and/or material choice for the adapter; the number of constrictors employed; and, the like. Thus, the preceding should be considered illustrative and not as limiting the scope of the following claims:

I claim:

1. A penile erection aid comprising a belt for encircling the lower torso region of the wearer, and a strap adapted to be looped around the base of the penis adjacent the torso and extending downwardly on each side of and coming together through an adjustment member under the scrotum, and thence extending side-by-side rearwardly and centrally upwardly within the space between the buttocks into connecting engagement with said belt, whereby said strap is tensioned in the region proximate the scrotum and the anus of the wearer exerting continuing pressure on said region and aiding the said penile erection.

2. The penile erection aid of claim 1 where independent constrictors placed on the erect penis serve an erection maintaining relationship.

3. The penile erection aid of claim 1 where an independent shield is provided having an opening through which said penis is inserted, serving support and directional aid purposes.

4. The penile erection aid of claim 1 where said strap is flexible and adaptable to define a concentrated and continual pressure on said region.

* * * * *